(12) United States Patent
Amarasekera et al.

(10) Patent No.: US 11,845,817 B2
(45) Date of Patent: Dec. 19, 2023

(54) COMPOSITIONS FOR SYNTHETIC POLYISOPRENE LATEX ARTICLES

(71) Applicant: Ansell Limited, Victoria (AU)

(72) Inventors: Koralalage Don Sugathananda Amarasekera, Kotte (LK); David M. Lucas, Selangor (MY); Angodage Sujith Ruwan Samantha Perera, Kelaniya (LK); Dambadeni Arachchige Ruwani Upekshika Lalanthani, Nainamadama (LK)

(73) Assignee: Ansell Limited, Victoria (AU)

( * ) Notice: Subject to any disclaimer, the term of this patent is extended or adjusted under 35 U.S.C. 154(b) by 612 days.

(21) Appl. No.: 16/975,173

(22) PCT Filed: Mar. 8, 2019

(86) PCT No.: PCT/AU2019/050211
§ 371 (c)(1),
(2) Date: Aug. 24, 2020

(87) PCT Pub. No.: WO2019/173863
PCT Pub. Date: Sep. 19, 2019

(65) Prior Publication Data
US 2021/0115172 A1 Apr. 22, 2021

Related U.S. Application Data

(60) Provisional application No. 62/641,340, filed on Mar. 10, 2018.

(51) Int. Cl.
*C08F 136/08* (2006.01)
*A41D 19/00* (2006.01)
(Continued)

(52) U.S. Cl.
CPC ........ *C08F 136/08* (2013.01); *A41D 19/0055* (2013.01); *A61F 6/04* (2013.01);
(Continued)

(58) Field of Classification Search
CPC .. C08F 136/00–04; C08F 136/08; C08L 9/00; C08L 9/10; C08L 2312/02
See application file for complete search history.

(56) References Cited

U.S. PATENT DOCUMENTS

2001/0051551 A1  12/2001  Maruoka
2004/0071909 A1*  4/2004  McGlothlin ............ B29C 41/14
                                                          428/36.8

(Continued)

FOREIGN PATENT DOCUMENTS

EP  3029100 A1  6/2016
GB  2 436 566 A  3/2007
(Continued)

OTHER PUBLICATIONS

Machine translation of JP2008285577A obtained from Patentscope. (Year: 2008).*

(Continued)

*Primary Examiner* — Kregg T Brooks
*Assistant Examiner* — David R. Foss
(74) *Attorney, Agent, or Firm* — Moser Taboada (57) ABSTRACT

The present disclosure relates to synthetic polyisoprene elastomeric articles including: one or more cured blend compositions of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent of the total (Continued)

amount of crosslinks in the cured blend composition. Methods of making synthetic polyisoprene elastomeric articles such as gloves or condoms is also disclosed.

20 Claims, 3 Drawing Sheets

(51) Int. Cl.
    *A61F 6/04*     (2006.01)
    *C08J 5/02*     (2006.01)
    *C08K 3/06*     (2006.01)
    *C08L 9/00*     (2006.01)
    *C08L 9/10*     (2006.01)
    *C08K 5/40*     (2006.01)
    *C08K 5/405*     (2006.01)

(52) U.S. Cl.
    CPC ............... *C08J 5/02* (2013.01); *C08K 3/06* (2013.01); *C08K 5/40* (2013.01); *C08K 5/405* (2013.01); *C08L 9/00* (2013.01); *C08L 9/10* (2013.01); *C08L 2201/52* (2013.01); *C08L 2205/02* (2013.01); *C08L 2312/02* (2013.01)

(56) References Cited

U.S. PATENT DOCUMENTS

| | | |
|---|---|---|
| 2004/0169317 A1 | 9/2004 | Wang et al. |
| 2009/0272384 A1 | 11/2009 | Lucas et al. |
| 2010/0267917 A1* | 10/2010 | Attrill ............... B29C 41/003 427/2.3 |
| 2012/0107485 A1 | 5/2012 | Chen et al. |
| 2015/0087761 A1 | 3/2015 | Satoh et al. |
| 2015/0272241 A1 | 10/2015 | Lucas et al. |

FOREIGN PATENT DOCUMENTS

| | | |
|---|---|---|
| JP | 2008285577 A * | 11/2008 |
| JP | 2011-519606 A | 7/2011 |
| JP | 2017-508840 A | 3/2017 |
| WO | WO 2004/033177 A1 | 4/2004 |

OTHER PUBLICATIONS

P. Boochathum et al., "Vulcanization of cis- and trans-polyisoprene and their blends: cure characteristics and crosslink distribution", European Polymer Journal 37, 2001, pp. 417-427.
International Search Report for Application No. PCT/AU2019/050211 dated Jul. 2, 2019.

* cited by examiner

COMPOSITIONS FOR SYNTHETIC POLYISOPRENE LATEX ARTICLES

CROSS-REFERENCE TO RELATED APPLICATIONS

This application claims the benefit of U.S. Provisional Application No. 62/641,340 under 35 USC 119(e), filed Mar. 10, 2018, herein incorporated by reference in its entirety.

BACKGROUND

Field of the Invention

The present disclosure relates to compounding synthetic polyisoprene and forming articles therefrom such as gloves or condoms. Embodiments of the present disclosure generally relate to polymeric compositions and, more particularly, to synthetic polyisoprene elastomeric compositions including blends of pre-vulcanized synthetic polyisoprene particles and non-prevulcanized synthetic polyisoprene particles wherein the blends are capable of being disposed as coatings on formers, cured, and creating articles such as gloves or condoms.

Description of the Related Art

Articles such as gloves or condoms are typically made from vulcanized natural rubber. The chemical name for natural rubber is polyisoprene and the monomer from which it is built is isoprene. Natural rubber has unique characteristics making natural rubber particularly useful for the preparation of barrier protection products. Among the unique characteristics of natural rubber is its high level of stereo-regularity, meaning polyisoprene is a chain like molecule comprised almost exclusively of cis-1,4 isoprene units. Natural rubber latex is also a highly branched polymer with a high molecular weight and a wide molecular weight distribution. The long chain length of polyisoprene also allows for entanglements, which may help hold a plurality of the chain like molecules together. Further, natural rubber is an excellent reactant for vulcanization processes such as sulfur vulcanization suitable for converting natural rubber to more durable materials by heating with sulfur or other curatives or accelerators. These characteristics of a base latex of natural rubber result in vulcanized rubber film products having a unique combination of strength and elasticity. However, natural polyisoprene and articles formed therefrom problematically includes natural proteins, some of which are known to produce Type I allergic reactions in some susceptible individuals.

Synthetic polyisoprene provides a material with the benefits of natural rubber and eliminates the potential for protein allergy e.g., in dip molded products. However, development of a true replacement for natural rubber has proved to be difficult, with synthetic variants, such as that produced by Kraton Inc. by anionic addition polymerization, having a lower level of stereo-regularity (i.e., less than 90% cis 1,4 isoprene) and reduced molecular weight characteristics. This molecular character, in turn, results in synthetic polyisoprene films having an inferior balance of properties compared to those of vulcanized natural rubber films. Further, the addition of one or more crosslinking agents to known synthetic polyisoprene compositions tends to problematically produce more inter-particle crosslinks and less intra-particle crosslinks during post-vulcanization, resulting in nonhomogeneous cure properties leading to latex film articles having poor strength and elongation properties, such as voids and cracks due to the formation of fractures in the inter-particle regions. In addition, synthetic polyisoprene latex problematically flocks easily, resulting in defects in dipped films for dip molded products, and a latex dip tank having a very limited lifetime.

Therefore, polymeric or elastomeric compositions such as synthetic polyisoprene films exhibiting crosslink variation for enhancing strength, elongation properties, tear resistance, homogenous curing, and aging properties and methods for manufacturing articles incorporating the coatings would represent an advance in the art. Further, polymeric or elastomeric compositions such as synthetic polyisoprene compositions that do not agglomerate or flock, have usable emulsion lifetimes, while reducing or eliminating health concerns relating to articles including N-nitrosamines and type IV allergens would represent an advance in the art.

SUMMARY

The present disclosure relates to a synthetic polyisoprene composition, article, and method of making as substantially shown in the figures and/or described herein, and as set forth more completely in the claims.

In embodiments, the present disclosure relates to a synthetic polyisoprene elastomeric article including: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent of the total amount of crosslinks in the cured blend composition. In some embodiments, the poly-sulfidic crosslinks are present in an amount of 64 to 76 percent of the total amount of crosslinks in the cured blend composition.

In some embodiments, the present disclosure relates to a method of making a synthetic polyisoprene article including: dipping a former into a polymeric, elastomeric, or latex coating composition comprising a blend of a synthetic polyisoprene material to form a layer atop the former, wherein the blend of a synthetic polyisoprene material comprises a pre-vulcanized polyisoprene component and non-prevulcanized polyisoprene component; and curing the layer to form a cured synthetic polyisoprene film with pre-vulcanized polyisoprene component and non-prevulcanized polyisoprene component bonded by mono-sulfidic and/or di-sulfidic, and poly-sulfidic crosslinks, wherein the poly-sulfidic crosslinks are present in an amount of 60 to 79 percent of the total amount of crosslinks in the film. In some embodiments, the poly-sulfidic crosslinks are present in an amount of 64 to 76 percent of the total amount of crosslinks in the film. In embodiments, the film or coating has enhanced tensile strength upon aging compared to its unaged value. In some embodiments, the method is suitable for forming a glove or condom. In embodiments, the glove or condom has a retained tensile strength of at least 95% after aging for at least seven days. In embodiments, the glove or condom includes a cured blend composition including pre-vulcanized synthetic polyisoprene particles present in an amount of 65 to 95 percent weight of the total blend composition and non-prevulcanized synthetic polyisoprene particles present in an amount of 5 to 35 percent weight of the total blend composition.

Various advantages, aspects and novel features of the present disclosure, as well as details of an illustrated embodiment thereof, will be more fully understood from the following description.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present disclosure relates to synthetic polyisoprene compositions, articles, and methods of making synthetic polyisoprene compositions and articles as substantially shown in and/or described herein. For example, in embodiments, the present disclosure relates to a synthetic polyisoprene elastomeric article including: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent of the total amount of crosslinks in the cured blend composition. In some embodiments, the poly-sulfidic crosslinks are present in an amount of 64 to 76 percent of the total amount of crosslinks in the cured blend composition. In embodiments, the polymeric or elastomeric compositions such as synthetic polyisoprene films of the present disclosure advantageously exhibit crosslink variation for enhancing strength, elongation properties, tear resistance, homogenous curing, and aging properties for films or coatings made therefrom. Further, in embodiments, the polymeric or elastomeric compositions such as synthetic polyisoprene compositions advantageously do not agglomerate or flock, have usable emulsion lifetimes, while reducing or eliminating health concerns relating to N-nitrosamines, type IV allergens, or natural proteins, some of which are known to produce Type I allergic reactions in some susceptible individuals.

In embodiments, the synthetic polyisoprene elastomeric articles of the present disclosure advantageously include in a cured blend composition having one or more of: an amount of poly-sulfidic crosslinks that is substantially retained upon aging; a crosslink density that increases by at least 20%, such as about 20% to about 30% upon aging; an average molecular weight between crosslinks in the amount of 8053 and 9711; tensile strength that increases upon aging; pre-vulcanized synthetic polyisoprene particles and non-prevulcanized synthetic polyisoprene particles bonded through intra-polyisoprene particle crosslinks and inter-polyisoprene crosslinks, wherein the amount of inter-polyisoprene crosslinks and crosslink density increases upon aging; and/or a crosslink density in the amount of $9.0 \times 10^{-5}$ to $12 \times 10^{-5}$ n mol/cm$^3$ prior to aging, an average molecular weight between crosslinks in the amount of about 9711 prior to aging, or an average molecular weight between crosslinks in the amount of about 8053 after aging, such as aging at 70 degrees Celsius for 7 days. In embodiments, compounding in accordance with the present disclosure advantageously varies the amount and type of crosslinks in the compositions upon aging compared to the unaged composition. For example, in embodiments, synthetic polyisoprene variants may include an increased amount of inter-molecular crosslinks while maintaining a homogenous cure and showing compositions and articles with increased tensile strength upon aging.

In embodiments, a synergistic effect in blending pre-vulcanized synthetic polyisoprene particles such as partially pre-vulcanized synthetic polyisoprene particles and non-prevulcanized synthetic polyisoprene particles has been discovered, which provides a composition having enhanced properties and other mechanical properties while remaining flexible when disposed as a coating or film formed on a former as an article such as a glove or condom. In embodiments, the composition blends also offer the advantages as described above.

Without intending to be bound to any theory, it is believed that in embodiments, the partially pre-vulcanized synthetic polyisoprene particles may be partially pre-vulcanized to a predetermined degree to vary the crosslink characteristics upon blending or mixing with non-prevulcanized synthetic polyisoprene particles of the present disclosure creating a polymer having a higher molecular weight, higher crosslink density, and retaining a higher number of poly-sulfidic crosslinks or sulfur crosslinks comprised of 3 or more (e.g., several) sulfur atoms affecting the physical properties of synthetic polyisoprene compositions and rubber compositions thereof, e.g., produce more inter-particle crosslinks, and improving tensile strength, tear strength, or fatigue properties. Therefore, in embodiments, the inclusion of partially pre-vulcanized synthetic polyisoprene particles in composition blends of the present disclosure promotes poly-sulfidic crosslinks to be present in an amount of 60 to 79 percent such as 64 to 76 percent of the total amount of crosslinks in a cured blend composition. Maintaining, substantially maintaining or increasing the poly-sulfidic crosslinks upon aging reduces or eliminates problems of overcure caused by inter-molecular crosslinks, and enables compositions with increased inter-molecular crosslinks suitable for forming articles such as gloves or condoms. The present disclosure advances over synthetic polyisoprene formulations where the absence of non-pre-vulcanized component blending into a pre-vulcanized component may promote the formation of predominantly intra-particle crosslinks thus particle integration during film formation at dipping and subsequent post vulcanization will have predominantly intra-particle crosslinks with reduced inter-particle crosslinks thus, during aging, oxidative reaction problematically occurs on the periphery of the particles and particularly crosslink cessation of long-chain sulfur crosslinks could result (such as loss of more than 30%, more than 15%, or more than 12% of the polysulfidic crosslinks), with subsequent overcure of the rubber film and loss of tensile strength over aging. It is believed that having more polysulfidic inter-particle crosslinks in the compositions and articles of the present disclosure, the inter-particle crosslinks rearrange and enhance the films tensile strength during aging. In embodiments of the present disclosure, the amount of the poly-sulfidic crosslinks in the cured blend composition is substantially retained upon aging, e.g., without a loss of more than 30%, more than 15%, or more than 12% of the polysulfidic crosslinks.

In embodiments, the present disclosure includes polymeric compositions comprising bends of pre-vulcanized synthetic polyisoprene particles and non-prevulcanized synthetic polyisoprene particles. In some embodiments, the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent of the total amount of crosslinks in the cured blend composition. In some embodiments, the pre-vulcanized synthetic polyisoprene particles and the non-prevulcanized synthetic polyisoprene particles are bonded by poly-sulfidic crosslinks present in an amount of about 64 to 76 percent of the total amount of crosslinks in the cured blend composition, about 70 to 75 percent of the total amount of crosslinks in the cured blend composition, about 69 percent, about 70 percent, about 71 percent, about 72 percent, about 73 percent, about 74 percent, about 75 percent, or about 76 percent of the total amount of crosslinks in the cured blend composition.

In some embodiments, the present disclosure provides a latex article that is formed by dipping a glove shaped former or condom shaped former into a pre-vulcanized synthetic polyisoprene latex emulsion, which is comprised of a blend composition of pre-vulcanized synthetic polyisoprene particles and non-prevulcanized synthetic polyisoprene particles. For example, in some embodiments, the pre-vulcanized synthetic polyisoprene latex emulsion is comprised of a pre-vulcanized polyisoprene component and non-prevulcanized polyisoprene component, blended together during the final compound preparation stage, after which the polyisoprene latex film is cured to produce the finished article. In some embodiments, a latex article such as a glove or condom is formed by dipping a coagulant coated glove or condom shaped former in a pre-vulcanized synthetic polyisoprene latex emulsion, which is comprised of a pre-vulcanized polyisoprene component and non-prevulcanized polyisoprene component, blended together during the final compound preparation stage, after which the coagulated polyisoprene latex film is cured to produce the finished article such as a glove or condom. One non-limiting example of synthetic polyisoprene latex suitable for use herein includes synthetic polyisoprene latex available from Kraton Polymers, which is produced by anionic polymerization with a high cis-1,4 content. In embodiments, the synthetic latex particles in the latex emulsion are pre-vulcanized by the incorporation of sulfur within and between the latex particles. This incorporation of sulfur within the synthetic latex particles may be accomplished by the methods described in U.S. Pat. Nos. 8,087,412 and 9,074,029 both to Lucas et al., and both herein incorporated by reference in their entireties. For example, incorporation of sulfur within the synthetic latex particles may be accomplished by one or more of: 1) using a sulfur emulsion that has a high content of soluble sulfur with $S_8$ ring structure; 2) the ring structure being disrupted or broken by catalytic activity of zinc dithiocarbamates, resulting in linear sulfur chains in the latex emulsion adapted for easy migration into the particles of synthetic polyisoprene in the latex emulsion; 3) using a potassium caprylate surfactant and sodium dodecyl benzene sulphonate (SDBS) surfactant in amounts sufficient and conditions suitable to wet the particles of synthetic polyisoprene in the latex emulsion such that chains of sulfur along with sulfur captured zinc dithiocarbamate is available for permeation into the synthetic latex particles; and 4) allowing sufficient time at selected process temperature in the range of 20 degrees Celsius to 35 degrees Celsius to progressively permeate sulfur into the synthetic polyisoprene particles.

In embodiments, sulfur permeation and pre-vulcanization may be validated by a Toluene Swelling Index (TSI) test. For example, in some embodiments, the partially pre-vulcanized synthetic polyisoprene particles may be partially pre-vulcanized to a predetermined degree determined using a Toluene Swelling Index (TSI) test such as a TSI test described below. In embodiments, the degree of pre-vulcanization of the pre-vulcanized component suitable for use herein is measured using TSI (Toluene Swell Index) and varies from 100% to 200%, or 110% to 200%. In some embodiments, the pre-vulcanized synthetic polyisoprene particles are vulcanized to a predetermined degree characterized by a toluene swelling index between 200% and 110%. In some embodiments, the cured blend composition is formed with partially pre-vulcanized synthetic polyisoprene particles characterized by a toluene swelling index between 110% and 200%, between 120% and 190%, between 130% and 170%, and between 140% to 160%. In some embodiments, the cured blend composition of the present disclosure is formed with partially pre-vulcanized synthetic polyisoprene particles characterized by a toluene swelling index of about 110%, about 120%, about 130%, about 140%, about 150%, about 160%, about 170%, about 180%, about 190% and about 200%.

In some embodiments, the percentage of blending of non-prevulcanized latex component into pre-vulcanized component may vary from 10% to 50% by total weight of the blend. In some embodiments, a blend composition comprises pre-vulcanized synthetic polyisoprene particles present in an amount of 65 to 95 percent weight of the total blend composition and non-prevulcanized synthetic polyisoprene particles present in an amount of 5 to 35 percent weight of the total blend composition. In some embodiments, a blend composition comprises pre-vulcanized synthetic polyisoprene particles present in an amount of 75 to 95 percent weight of the total blend composition and non-prevulcanized synthetic polyisoprene particles present in an amount of 5 to 25 percent weight of the total blend composition. In some embodiments, a blend composition comprises pre-vulcanized synthetic polyisoprene particles present in an amount of 85 to 95 percent weight of the total blend composition and non-prevulcanized synthetic polyisoprene particles present in an amount of 5 to 15 percent weight of the total blend composition. In some embodiments, a blend composition comprises pre-vulcanized synthetic polyisoprene particles present in an amount of 65 to 95 phr and non-prevulcanized synthetic polyisoprene particles present in an amount of 5 to 35 phr of the total blend composition.

In some embodiments, a blend composition comprises or consists of pre-vulcanized synthetic polyisoprene particles present in an amount of 65 to 95 percent weight of the total blend composition and non-prevulcanized synthetic polyisoprene particles present in an amount of 5 to 35 percent weight of the total blend composition, wherein the degree of pre-vulcanization of the pre-vulcanized component or particles thereof is 100% to 250% measured using TSI (Toluene Swell Index).

In some embodiments, the rate of pre-vulcanization is predetermined. For example, embodiments may include facilitating a slow rate of pre-vulcanization so as to prevent peripheral vulcanization on the boundaries of an aggregate of polyisoprene latex particles, and latex such that pre-vulcanized particles or constituent may be blended with non-prevulcanized synthetic latex or particles thereof to enhance inter-particle crosslinks. In embodiments, non-prevulcanized latex or particles thereof help the mobility of molecules in a significantly less pre-vulcanized component or particles thereof during post-vulcanization. In embodiments, the inclusion of pre-vulcanized synthetic polyisoprene particles or partially pre-vulcanized synthetic polyisoprene particles and non-prevulcanized synthetic polyisoprene particles, enhance the tensile properties by forming more inter-particle crosslinks and/or mitigating a potential oxidative reaction effect on the periphery of the polyisoprene particles (on the boundaries of aggregates of particles) which may result in loss of tensile over elevated temperature aging or extended real-time aging conditions.

In some embodiments, compositions of the present disclosure for use in a prevulcanized or partially prevulcanized component of the present disclosure comprise one or more vulcanizing agents, activators, accelerators, anti-oxidants, or surfactants/emulsifiers/or wetting agents, and combinations thereof.

In some embodiments, compositions of the present disclosure for use in a prevulcanized or partially prevulcanized component of the present disclosure comprise one or more vulcanizing agents. Non-limiting examples of vulcanizing agents include synthetic polyisoprene latex in an amount of 100 phr, sulfur in an amount of 0.5 to 3.0 phr, dipentamethylene thiuram polysulphide/diphenyl thiourea in an amount of 0.00 to 0.5 phr, or 0.1 to 0.5 phr, tetrabenzyl thiuram disulphide/diphenyl thiourea in an amount of 0.00 to 0.5 phr, or 0.1 to 0.5 phr, n-tert butylbenzothiazole 2-sulphenamide/tetraethylthiuram disulphide in an amount of 0.00 to 0.5 phr, or 0.1 to 0.5 phr.

In some embodiments, compositions of the present disclosure for use in a prevulcanized or partially prevulcanized component of the present disclosure comprise one or more activators such as active ZnO in an amount such as 0.2 to 1.0 phr.

In some embodiments, compositions of the present disclosure for use in a prevulcanized or partially prevulcanized component of the present disclosure comprise one or more accelerators. Non-limiting examples of suitable accelerators include one or more of zinc diethiocarbamate/zinc dibutyldithiocarbamate/zinc diisononyle dithiocarbamate in an amount of 0.1 to 1.0 phr, zinc-2-mercaptobenzothiazole/sodium dibutyldithiocarbamate in an amount of 0.01-0.50 phr, diisopropyl xanthogen polysulphide in an amount of 0.10-0.60 phr, n-tert butylbenzothiazole 2-sulphenamide in an amount of 0.00 to 0.3 phr or 0.1 to 0.3 phr. Non-limiting examples of suitable accelerators further include one or more of zinc diethiocarbamate/zinc dibutyldithiocarbamate in combination with ZDNC in an amount of 0.10 to 1.00 phr, zinc-2-mercaptobenzothiazole/sodium dibutyldithiocarbamate/zinc diisononyle dithiocarbamate in an amount of 0.10 to 1.00 phr, and/or diisopropyl xanthogen polysulphide in an amount of 0.10-0.60 phr. Non-limiting examples of suitable accelerators further include one or more of zinc diethiocarbamate/zinc dibutyldithiocarbamate in an amount of 0.10 to 1.00 phr, zinc-2-mercaptobenzothiazole/sodium dibutyldithiocarbamate in an amount of 0.10 to 1.00 phr, and/or diisopropyl xanthogen polysulphide in an amount of 0.10-0.60 phr. In some embodiments, non-limiting examples of accelerators for use herein further include zinc dithiocarbamate or a zinc complex of dithiocarbamate, zinc dimethyldithiocarbamate, zinc diethyl dithiocarbamate, zinc dibutyldithiocarbamate, zinc diisononyl dithiocarbamate, and combinations thereof. In some embodiments, Arbestab Z brand zinc diisononyldithiocarbamate may be included as a non-limiting example of an accelerator as described herein. Arbestab Z is an accelerator with high molecular weight (754.4 g/mol) based on the highly branched and longer alkyl chain secondary amine. In embodiments, the Arbestab Z brand accelerator is highly involatile, thermally stable and soluble in rubbers. In embodiments, Arbestab Z is a higher alkyl dithiocarbamate of zinc. Zinc diisononyldithiocarbamate, CAS [84604-96-6], molecular formula $C_{38}H_{76}N_2S_4ZN$, may be commercially available from Robinson Brothers Limited, Phoenix Street, West Bromwich, West Midlands, England. In embodiments, zinc diisononyldithiocarbamate may be incorporated into compositions such as latex emulsions of the present disclosure suitable for forming articles such as a condom or glove of the present disclosure.

In some embodiments, compositions of the present disclosure for use in a prevulcanized or partially prevulcanized component of the present disclosure comprise one or more derivatives of thiourea such as DPTU or thiazole such as n-tert butylbenzothiazole 2-sulphenamide (TBBS) accelerators or xanthogen or higher molecular weight dithiocarbamate. In embodiments, one or more accelerators may be used alone or in combination and provided in an amount sufficient to slow down the formation of a sulfur captured accelerator complex and prevent fast peripheral vulcanization, as that would otherwise significantly reduce intra-particle crosslink formation by impeding sulfur captured accelerator particles migrating into the latex particles, required for substantially uniform intra-particle crosslink formation and higher tensile strength.

In some embodiments, the non-prevulcanized component or particles thereof may be blended into pre-vulcanized component or particles when the TSI (toluene swell index) of the pre-vulcanized component reaches 250-100%, for example an amount sufficient to form crosslink structures comprised of long-chain and short chain sulfur crosslinks. In embodiments, a TSI (toluene swell index) of 250-100% of the pre-vulcanized component allows crosslink rearrangement on aging, further enhancing tensile strength compared to its unaged value. In some embodiments, where xanthogen and dithiocarbamate accelerator combination are used, the pre-vulcanization temperature of the prevulcanized component shall be kept relatively low, for example in the range of 20-35 degrees Celsius in order to achieve the required level and type of crosslinks.

In some embodiments, e.g. where thiazole/thiuram or combination thereof is used in pre-vulcanization, the pre-vulcanization temperature can be controlled at 15 degrees Celsius. In some embodiments, partially prevulcanized particles or polyisoprene particles from the prevulcanized component are suitable for use herein when they are no longer very tacky but exhibits lesser degree of tackiness with an isopropanol index of 2.0-2.5 or TSI (toluene swell index) of 100-250%.

In some embodiments, a synthetic polyisoprene latex emulsion suitable for use herein may include crosslinking agents. Non-limiting examples of suitable crosslinking agents include sodium dibutyldithiocarbamate (SDBC), tetra benzyl thiuram disulphide, diisopropyl xanthogen, tetraethylthiuram disulphide, dipentamethylene thiuram polysulphide, xanthogen sulphide, and compositions thereof. In embodiments, crosslinking agents are provided in an amount sufficient for curing the inter-particle regions during the vulcanization or cure cycle. These accelerators can be used in combination or alone with thiazole, TBBS/Thiuram or thiourea/thiuram accelerator systems.

In the non-prevulcanized component or composition including non-prevulcanized synthetic polyisoprene particles, insoluble sulfur such as amorphous sulfur or polysulfur present in the sulfur dispersion added to the polyisoprene latex emulsion becomes soluble at post-vulcanization cure temperatures of 100° C. to 150° C. and reacts with the zinc dithiocarbamate accelerator or other accelerators, vulcanizing inter-particle regions between the prevulcanized polyisoprene particles. During post vulcanization, partially pre-vulcanized synthetic polyisoprene particles with the permeated sulfur, also cure completely in the intra-particle regions, while the largely non-pre-vulcanized latex component also cured in the high-temperature post vulcanizing temperature, achieving a TSI index of the completely cured film in the range of 70 to 80%, 72-78% or about 75%.

Figure 1A:
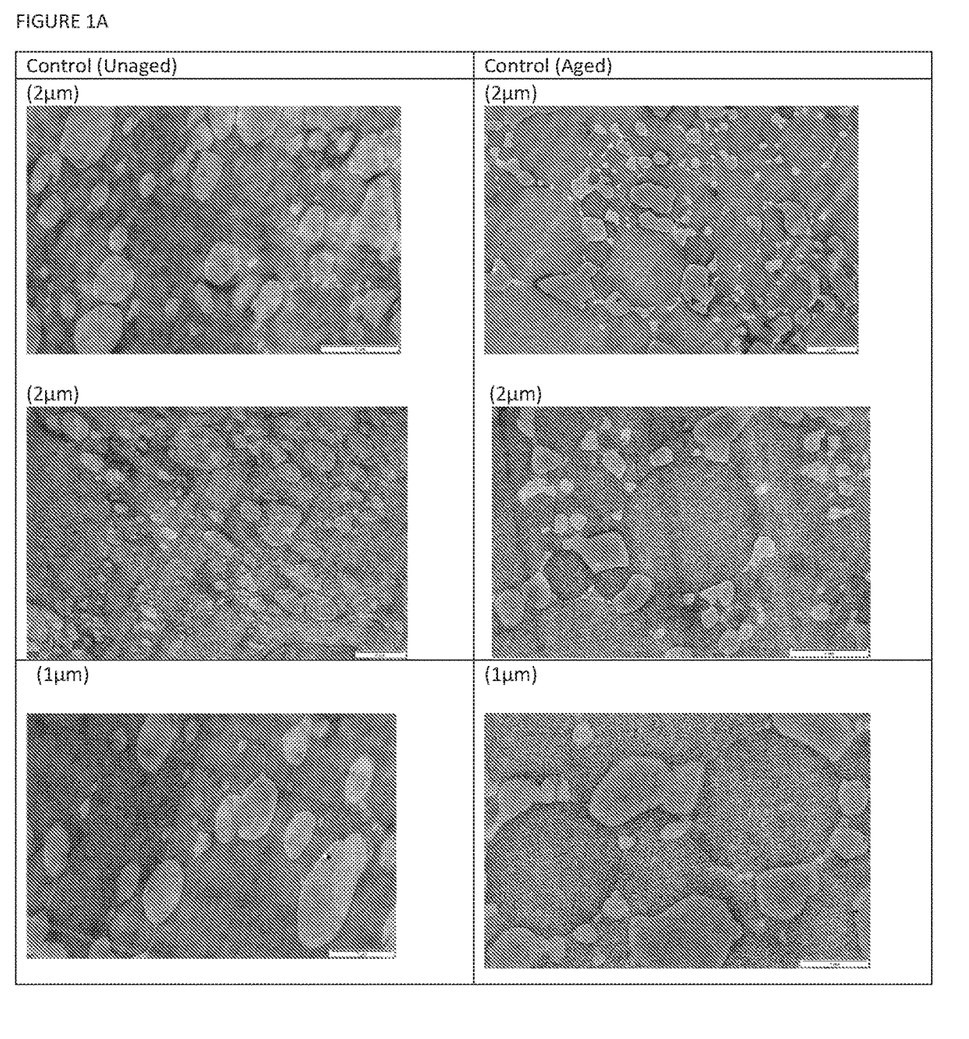
FIGS. 1A and 1B show transmission electron micrographs of osmium tetroxide treated polyisoprene control latex film and osmium tetroxide treated polyisoprene latex film prepared in accordance with the present disclosure.
Figure 1B:
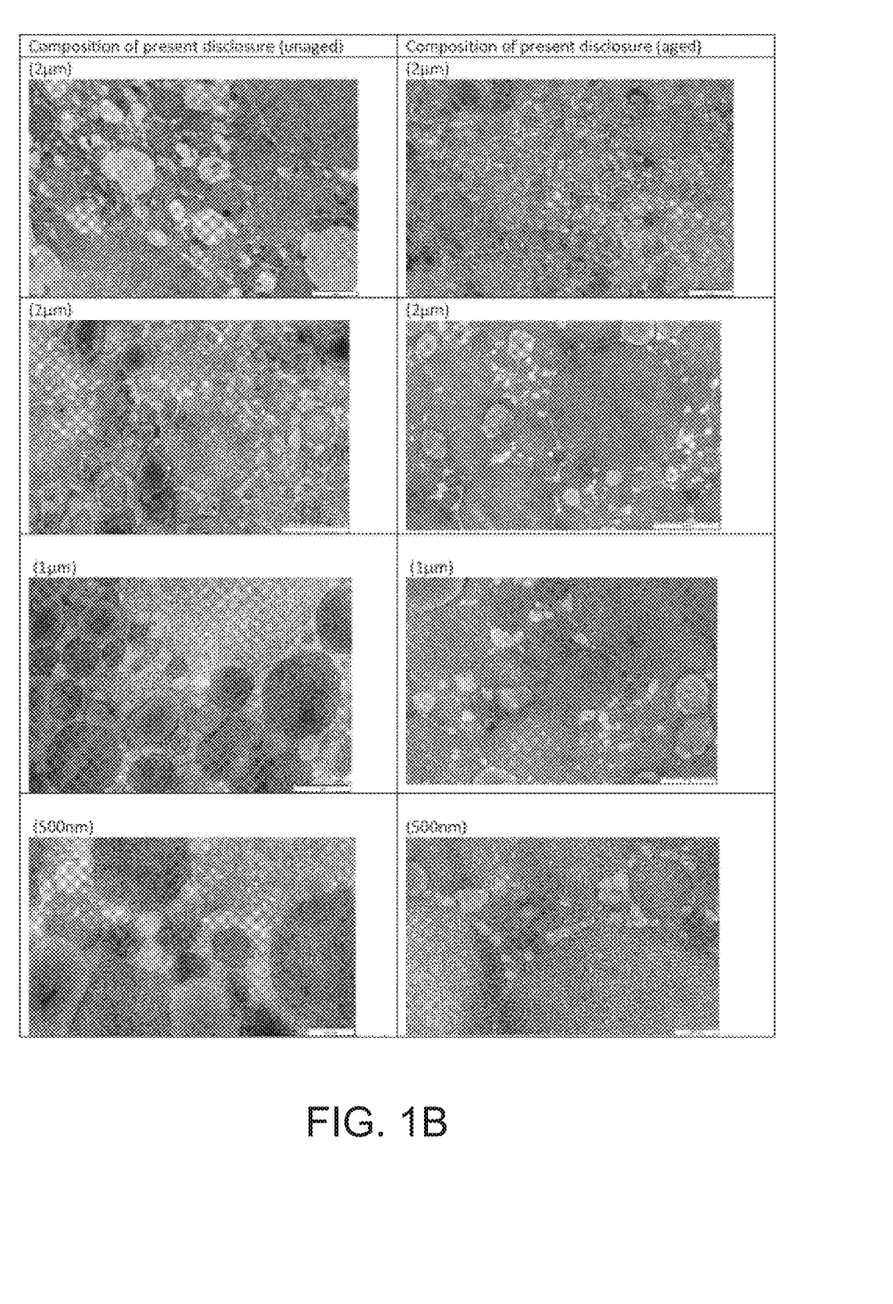

In embodiments, the products or articles such as gloves or condoms formed in accordance with the present disclosure have several distinguishing features that have imprints of this pre-vulcanization and post-vulcanization methodology with improved inter-particle crosslinks over semi-prevulcanized latex film completely cured in post-vulcanization setting. For example, when examined using osmium stained transmission electron micrograph (TEM), after swelling, polymerization and fixation in styrene, shows intra polyisoprene particle crosslink structure, separated by increased regions of uniform crosslinking without particle structure (inter-particle regions) and reduced evidence of polyisoprene voids in the transmission electron micrograph TEM, compared to prior art polyisoprene films. The polyisoprene films thus produced in accordance with the present disclosure show improved tensile strength, and there is an increased amount of poly-sulphidic nature of crosslinks and inter-particle crosslinks. In embodiments, films show a lower level of crosslinking in the unaged film (coming from the non-prevulcanized part of the latex blend), but as the film ages the crosslink density increases providing improved film durability with aging. FIG. 1A shows transmission electron micrographs of osmium tetroxide treated polyisoprene control latex film (prepared without a blend composition of pre-vulcanized synthetic polyisoprene particles and non-prevulcanized synthetic polyisoprene particles as described herein) with the scale bars expressed in micrometers such as 1 micrometer and 2 micrometer. FIG. 1B shows transmission electron micrographs of osmium tetroxide treated polyisoprene latex film prepared in accordance with the present disclosure (with scale bar expressed in micrometers such as 1 micrometer and 2 micrometer and 500 nanometers).

In some embodiments, methods for producing synthetic polyisoprene products comprises the use of a synthetic polyisoprene latex emulsion that includes a composition for both pre and post vulcanization, along with conventional latex emulsion additives including stabilizers, pH control agents, antioxidants, preservatives etc. In embodiments, a first phase produces pre-vulcanized synthetic polyisoprene particles such as partially pre-vulcanized synthetic polyisoprene. In embodiments, the first phase formulation includes pre-vulcanized synthetic polyisoprene particles vulcanized to a pre-determined degree such as a formulation characterized as having a TSI (toluene swell index) of 100-200%, or in embodiments, 110% to 200%. In embodiments, the first phase formulations comprises synthetic polyisoprene, sulphur dispersion, active ZnO, one or more activators and other constituents as described herein. In embodiments, the first phase formulation is formulated and then, in a second phase combined or mixed into a formulation including synthetic polyisoprene characterized as non-prevulcanized. In embodiments, the synthetic polyisoprene characterized as non-prevulcanized comprises potassium hydroxide, active ZnO (0.1 to 1.0 parts by weight), ammonia, and optionally a green pigment. In embodiments, the second phase compounds the pre-vulcanized synthetic polyisoprene particles and synthetic polyisoprene characterized as non-prevulcanized, forming an emulsion suitable for being contacted with a former for forming a film thereon. The film may subsequently be cured and/or vulcanize to form a post vulcanization composition or an article of the present disclosure.

In some embodiments, the synthetic polyisoprene particles suitable for use herein (in the pre-vulcanized synthetic polyisoprene particles and synthetic polyisoprene characterized as non-prevulcanized) include cis-1,4-polyisoprene having a diameter in the range of about 0.2 to 2 micrometers, and maintained in an aqueous medium of a latex emulsion. In embodiments, Kraton® 'IR-KP401A' latex is supplied by Kraton Polymers Group, 15710 John F. Kennedy Blvd., Suite 300, Houston, Tex. 77032 is suitable for use in accordance with the present disclosure. In embodiments, the pre-vulcanization of the synthetic latex particles in the latex emulsion occurs over a period of time between 35 hours to over 4 days depending on the temperature of the latex emulsion which is generally controlled in the range of 20° C. to 35° C. In embodiments, the degree of pre-vulcanization of the synthetic latex particles is monitored by toluene or isopropanol index or both tests and the latex particles progress from a very tacky feel (TSI of 250% or IPA Index of 1.0) to a lesser degree of tacky feel (TSI of 110% or IPA index of 3). In some embodiments, a typical synthetic polyisoprene latex emulsion composition is provided in terms of 100 parts by weight of dry rubber (phr).

In some embodiments, the pre-vulcanized synthetic polyisoprene component or particles thereof include accelerator packages such as ZDEC and/or ZDBC, DPTU, TBBS, thiuram, ZDNC accelerator, SDBC accelerator, DXP accelerator together with reactive zinc oxide activator, with a total accelerator content in the range of 0.2 to 2.5 phr. In some embodiments, the surfactant package includes potassium caprylate, sodium dodecyl benzene sulphonate and polyoxyethylene cetyl/stearyl ether with surfactants in the range of 0.3 to 1.5 phr. In some embodiments, the surfactant package includes Winsgtay L or butylated reaction product of p-cresol & dicyclopentadiene anti-oxidant preservative is in the range of 0.3 to 2.5 phr, ammonium hydroxide is in the range of 0 to 0.36 phr. In embodiments, during pre-vulcanization sulfur crosslinking takes place within the latex particles (intra-particle) in the aqueous synthetic polyisoprene emulsion itself vulcanizing the intra-particle regions and then the entire particle of synthetic polyisoprene is crosslinked during post-vulcanization cure cycle. During post-vulcanization crosslinking takes place between the particles as well as within the particles of synthetic polyisoprene thus forming a coherent latex film through the curing cycle.

In some embodiments, the pre-vulcanized synthetic polyisoprene component or particles thereof include soluble sulfur, such as $S_8$ rings of sulfur, catalyzed by a zinc complex of dithiocarbamate in combination with potassium caprylate and sodium dodecyl benzene sulphonate (SDBS) surfactant. This is done to create pre-vulcanized synthetic polyisoprene particles in a latex composition which is partly blended with un-vulcanized polyisoprene synthetic latex upon achieving pre-determined degree of pre-vulcanization of the pre-vulcanized component of the blend. The degree of pre-vulcanization of the pre-vulcanized component of the blend is formed in order to influence more inter-particle crosslinking and molecular interaction between latex particles during post vulcanization as mobility of polymer molecules in the un-vulcanized component of the blend readily occurs thus forming stronger inter-particle crosslinks and interaction of molecules. This enhances the tensile strength upon curing of the film formed at dipping.

In embodiments, latex composition prepared in accordance with the present disclosure enables the production of latex film articles by dipping coagulant coated formers into the composition. In embodiments, the composition for dipping includes a surfactant package sufficient to inhibit synthetic polyisoprene particle agglomeration and flocculation. The latex dipped film has synthetic polyisoprene particles that become crosslinked and regions between the particles are crosslinked during the post-vulcanization curing, forming both intra-crosslinked and inter-crosslinked bonds. The articles that result such as gloves and condoms comprise a high quality and uniform latex film. In embodiments, the latex-stabilizing composition is one that keeps the particles of synthetic polyisoprene separated from each other in the aqueous medium. Since the polyisoprene particles do not touch each other, they are unable to agglomerate and flock. This is important because, once the particles begin to agglomerate, the particles may never be separated due to Vanderwaals forces. In embodiments, the latex-stabilizing composition comprises a surfactant package comprising at least one surfactant. An anionic surfactant may be used, especially one that can be stably maintained for a period of well over one month and up to two months or more. An example of such a surfactant is sodium dodecyl benzene sulphonate (SDBS). Other examples include, but are not limited to, other alkyl aryl sulphonates, alkyl sulphonates, oleic sulphonates (e.g., C14 oleic sulphonate, which is sold under the trade name CalsoftAOS-40 (Pilot Chem. Co., Red Bank, N.J.), and alcohol sulphate (e.g., sodium lauryl sulphate). SDBS or another alkyl aryl sulphonate and may be present in an amount of about 0.1-0.35 Wt %, based on the dry weight of the polyisoprene or 0.1 to 0.35 phr. SDBS or another alkyl aryl sulphonate can be combined with one or more other surfactants, such as potassium caprylate, polyoxyethylene cetyl/stearyl ether, and the like. For example, SDBS or another alkyl aryl sulphonate can be combined with potassium caprylate, alone or in further combination with polyoxyethylene cetyl/stearyl ether, when SDBS or alkyl aryl sulphonate is used in combination with one or more other surfactants. In embodiments each surfactant is present in an amount of about 0.05-1.2 Wt %, based on the dry weight of the polyisoprene or 0.05 to 1.2 phr, and the total amount of the surfactant package is about 0.4-1.2 Wt %, based on the dry weight of the polyisoprene. In embodiments, when SDBS or another alkyl aryl sulphonate is used in combination with potassium caprylate and polyoxyethylene cetyl-stearyl ether, the polyoxyethylene cetyl-stearyl ether is present in an amount of about 0.1-0.5 Wt %, based on the dry weight of the polyisoprene.

In view of the above, the present disclosure provides a surfactant-stabilized, pre-vulcanized or partially pre-vulcanized (having a Toluene Swell Index of 100-250 percent), and un-vulcanized blend of synthetic polyisoprene latex composition. In embodiments, the TSI index measures the extent of swelling of the test piece (e.g. 2.1 cm in diameter) in toluene over 1 hr period in room temperature with respect to its original diameter of the test piece. A TSI test is provided below suitable for showing the degree of pre-vulcanization of the latex. As for Toluene Swelling Index (TSI) above 250 means it is less pre-vulcanized and below 100 means the lower limit for suitability of latex for dipping. The pre-vulcanization rate of the pre-vulcanized or partially pre-vulcanized component is monitored as to ensure that it is ready for mixing with non-prevulcanized synthetic polyisoprene to form a synthetic latex emulsion ready for dipping and forming synthetic polyisoprene gloves or condoms. In some embodiments, the pre-vulcanization composition includes potassium caprylate and SDBS or another alkyl aryl sulphonate surfactants with zinc dithiocarbamate, and soluble sulfur. In embodiments, the latex emulsion with surfactants wets the synthetic polyisoprene particles and catalytic action of zinc dithiocarbamate breaks the ring of soluble S8 molecule forming linear chain of soluble sulfur pre-vulcanizing particles of synthetic polyisoprene.

In embodiments, the post-vulcanization composition formed of a blend of pre-vulcanized and un-vulcanized components has sulfur and other accelerators that cause inter-particle crosslinking during post-vulcanization. Such crosslinking results in more homogeneous latex having greater strength and elongation properties and crosslink density. In some embodiments, the pre-vulcanizing composition comprises (i) a crosslinking package comprising zinc diethyldithiacarbamate or zinc dibutyldithiocarbamate or any other derivatives of thiocarbamate, zinc-2-mercaptobenzothiazole or its derivatives, diisopropyl xanthogen polysulphide or its derivative, zinc and DPTU and/or TBBS accelerators and soluble sulfur (ii), and a wetting agent. During pre-vulcanization, sulfur with its ring structure broken by the catalytic action of zinc dithiocarbamate accelerator penetrates the polyisoprene particles and initially interacts with the isoprene double bonds therein. It is recognized that, unlike the S8 rings of soluble sulfur, amorphous or polymeric sulfur are not soluble. However amorphous or polymeric sulfur becomes soluble at 120 C., which is at or near the latex cure temperature, thus insoluble or polymeric sulfur remain outside synthetic polyisoprene particles in the latex emulsion and facilitates crosslinking of inter particle regions. According to embodiments of the present disclosure, diffusion of sulfur into synthetic polyisoprene particle requires sulfur to be soluble. The wetting agents used in accordance with the present disclosure may facilitate wetting of the polyisoprene particles and brings soluble sulfur with ring structure broken by zinc dithiocarbamate catalytic action into contact with the surface of the polyisoprene particles and permeation of sulfur occurs during processing time provided. In some embodiments, the incorporation of ZMBT which has a synergistic effect with ZDEC renders the particle to have higher crosslink density thereby increasing the extent of crosslink formation within intra and inter-particle crosslinks, predominantly during the post-vulcanization reaction. Also zinc dithiocarbamate or diisononyl or dibutyl dithiocarbamate in conjunction with xanthogen disulphide could pre-vulcanize latex at elevated temperature in the range of 30–50° C., and the latex can be post-vulcanized in the temperatures between 100° C. to 150° C.

The pre-vulcanized structure of the aqueous latex emulsion is stable for several days, e.g., up to 5 days. In embodiments, sulfur is present in the synthetic polyisoprene latex emulsion in an amount of about 0.8-3.0 Wt %, based on the dry weight of polyisoprene. If zinc oxide is used, it may be present in an amount of about 0.01-0.75 Wt %, based on the dry weight of polyisoprene. Examples of suitable wetting agents include, but are not limited to, salts (e.g., sodium salt or potassium salt) of fatty acids, which are anionic, e.g., sodium stearate, sodium oleate, and potassium caprylate. Potassium caprylate is advantageously used with a salt of a short-chain fatty acid, SDBS and polyoxyethylene cetyl/stearyl ether. The penetration of the components of the pre-vulcanizing composition into the polyisoprene particles is a strong function of the polyisoprene particle size and size distribution.

Typically, smaller particles have a larger surface area, and the components of the pre-vulcanizing composition penetrate these small particles more rapidly. However, these larger surface areas result in more inter-particle regions, which are crosslinked by the crosslinking agent during post-vulcanization. In contrast, larger particles have a smaller surface area, and the components of the pre-vulcanizing composition penetrate these large particles more slowly. The smaller surface areas result in less inter-particle regions. Aggregates of smaller particles appear like a large particle, which behaves differently than a large particle. Therefore, there is a delicate balance in selecting the size and size range distribution of the polyisoprene particles to produce optimal strength properties that balance pre-vulcanization intra-particle crosslinking with post-vulcanization inter-particle crosslinking. As indicated above, particles in the range of about 0.2-2 micrometers provide optimal results. The penetration of the components of the pre-vulcanizing composition into the polyisoprene particles is also a function of the diffusion process, itself, which is a linear function of time and an exponential function of temperature, resulting in a thermally activated process. Therefore, increasing the temperature by a few degrees during the pre-vulcanization step increases significantly the pre-vulcanization rate. For example, pre-vulcanization at room temperature requires from about 2-5 days or as much as about 9 days, while pre-vulcanization at an elevated temperature, e.g., about 50-70 degrees Celsius, requires only about 3-7 hours. However a faster rate of pre-vulcanization is avoided in order to promote the right balance between inter and intra particle crosslinking and therefore a pre-vulcanization temperature would be 15 to 35 degrees Celsius with the pre-vulcanization time ranging from min 20 hrs to more than 4 days. In embodiments, the post-vulcanization composition comprises sodium dibutyl dithiocarbamate (SDBC), sulfur, a thiuram compound, and/or a xanthogen compound, alone or in further combination with a surfactant. Examples of suitable xanthogens include, but are not limited to, diisopropyl xanthogen polysulphide (DXP), diisopropyl xanthogen, tetraethylthitaiuram disulphide, and xanthogen sulphide. In embodiments, DXP is a xanthogen suitable for use herein. An example of a thiuram compound is tetrabenzylthiuram disulphide, dipentamethylene thiuram polysulphide. The post-vulcanization composition is one that causes inter-particle crosslinking upon activation at the elevated temperature (e. g., 100-150° Celsius). In addition, this post-vulcanization cure also crosslinks the synthetic polyisoprene particles with permeated sulfur. Such crosslinking results in a more homogeneous latex film having greater strength and elongation properties. In embodiments, a method comprises adding a latex-stabilizing composition, such as one comprising a surfactant package comprising at least one surfactant, such as at least one surfactant selected from the group consisting of an alkyl aryl sulphonate (e. g., SDBS), an alkyl sulphonate (e.g., olein sulphonate) and an alcohol sulphate (e.g., sodium lauryl sulphate). SDBS can be combined with potassium caprylate, alone or with polyoxyethylene cetyl/stearyl ether. In embodiments, a surfactant package comprises SDBS, potassium caprylate, and polyoxyethylene cetyl/stearyl ether. Upon addition of the latex stabilizing composition, the emulsion is stirred, to keep the polyisoprene particles from touching each other. Then, the method comprises the steps of adding a pre-vulcanization composition to formulate a synthetic polyisoprene latex emulsion. In embodiments, the pre-vulcanization composition may include (a) a zinc dithiocarbamate selected from zinc diethyldithiocarbamate and zinc dibutyldithiocarbamate or zinc diisononyle dithiocarbamate and combinations thereof; (b) sulfur, e.g, with high S8 content and (b) a wetting agent. In embodiments, the wetting agent may be a salt of a fatty acid, such as sodium stearate, sodium oleate, or potassium caprylate. The aqueous latex emulsion is stirred and periodically examined for permeation of pre-vulcanization agents into the synthetic polyisoprene particles by using the isopropanol and TSI index test. The reason why this sequence is adopted is because the polyisoprene latex has an inherent tendency to flock and 'case harden' due to peripheral reaction with sulfur catalyzed by ZDBC or ZDEC. This has to be prevented so that tightly bonded particles do not result. The presence of surfactants and creation of opened out S8 chains of sulfur enables the diffusion of sulfur into the particles. The method further comprises the steps of adding post vulcanization composition to the synthetic polyisoprene latex emulsion with accelerators selected from the group consisting of SDBC, reactive zinc oxide, sodium diethyldithiocarbamate, sodium dibutyldithiocarbamate, thiuram such as dipentamethylene thiuram polysulphide (P25) and xanthogen. If reactive zinc oxide is present, it may be present in an amount of about 0.1 to 1.0 Wt %, based on the dry weight of polyisoprene. The thiuram can be tetraethylthiuram disulphide, tetrabenzyl thiuram disulphide. The xanthogen can be DXP, diisopropyl xanthogen, or xanthogen sulphide. The composition thus produced is stable for up to about 5 days at 10° Celsius to 25° Celsius and can be used in a production line. Table 1-3 below shows examples of compositions that exhibits this pre-vulcanization behavior.

Three exemplary embodiments of compositions according to the present disclosure suitable for forming a pre-vulcanized polyisoprene component or pre-vulcanized synthetic polyisoprene particles are show in Tables 1-3. It is to be understood that the compositions need not contain each ingredient. These compositions are suitable for combining with synthetic polyisoprene and compositions thereof characterized as non-prevulcanized to form a pre-vulcanized dipping composition in accordance with the present disclosure. The compositions of Tables 1-3 may be provided in an amount of 65 to 95 percent weight of a total blend composition and mixed with non-prevulcanized synthetic polyisoprene particles present in an amount of 5 to 35 percent weight of the total blend composition. In embodiments, the blend compositions are characterized as pre-vulcanized compositions suitable for being contacted with a former for making dip coated films. The films may be cured and vulcanized to make articles in accordance with the present disclosure.

TABLE 1

| chemical name | Other names | Amount in parts per hundred rubber (phr) |
|---|---|---|
| Vulcanizing agent (chemical type) | | |
| Polyisoprene Latex | IR-KP 401Kraton Latex | 100 |

TABLE 1-continued

| chemical name | Other names | Amount in parts per hundred rubber (phr) |
|---|---|---|
| Sulphur | | 0.50-3.00 |
| Dipentamethylene thiuram polysulphide/Diphenyle thiourea | Robac P25/DPTU | 0.00-0.50 |
| Activator (chemical type) | | |
| Active ZnO | ZnO | 0.10-1.00 |
| Accelerators (chemical type) | | |
| Zinc diethiocarbamate/Zinc dibutyldithiocarbamate/Zinc diisononyle dithiocarbamate | ZDEC/ZDBC/ZDNC | 0.10-1.00 |
| Zinc-2-mercaptobenzothiazole/Sodium dibutyldithiocarbamate | ZMBT/SDBC | 0.01-0.50 |
| Diisopropyl xanthogen polysulphide | | 0.10-0.60 |
| n-tert butylbenzothiazole 2-sulphenamide | TBBS | 0.00-0.30 |
| Anti-oxidants (chemical type) | | |
| 4 & 5 methyl-2-mercaptobenzimidazole/Butylated p-cresol & dicyclopentadiene | | 0.80-2.5 |
| Surfactants/emulsifiers/wetting agents | | |
| Sodium salts of naphthalenesulphonic acid/Sodium lauryl sulfate | | 0.10-0.80 |
| Sodium linear alkylbenzene sulfonate/Potassium caprylate | | 0.10-1.00 |
| Sodium linear alkyl benzene sulfonate & sodium lauryl ether sulfate | Teepol LD I-21 | 0.01-0.10 0.00-0.10 |

TABLE 2

| Chemical name | Other names | Amount in parts per hundred rubber (phr) |
|---|---|---|
| Vulcanizing agent (Chemical type) | | |
| Polyisoprene Latex | IR-KP 401Kraton Latex | 100 |
| Sulphur | | 0.50-3.00 |
| tetrabenzyl thiuram disulphide/Diphenyle thiourea | DPTU | 0.00-0.50 |
| Activator (Chemical type) | | |
| Active ZnO | ZnO | 0.10-1.00 |
| Accelerators (Chemical type) | | |
| Zinc diethiocarbamate/Zinc dibutyldithiocarbamate | ZDEC/ZDBC | 0.10-1.00 |
| Zinc-2-mercaptobenzothiazole/Sodium dibutyldithiocarbamate/Zinc diisononyle dithiocarbamate | ZMBT/SDBC/ZDNC | 0.01-0.50 |
| Diisopropyl xanthogen polysulphide | | 0.10-0.60 |
| Anti-oxidants (Chemical type) | | |
| 4 & 5 methyl-2-mercaptobenzimidazole/Butylated p-cresol & dicyclopentadiene | | 0.80-2.5 |
| Surfactants/Emulsifiers/Wetting agents (Chemical type) | | |
| Sodium salts of naphthalenesulphonic acid/Sodium lauryl sulfate | | 0.10-0.80 |
| Sodium linear alkylbenzen sulfonate/Potassium caprylate | | 0.10-1.00 |
| Sodium linear alkyl benzene sulfonate & sodium lauryl ether sulfate | Teepol LD I-21 | 0.01-0.10 0.00-0.10 |

TABLE 3

| Chemical name | Other names | Amount in parts per hundred rubber (phr) |
|---|---|---|
| Vulcanizing agent (Chemical type) | | |
| Polyisoprene Latex | IR-KP 401Kraton Latex | 100 |
| Sulphur | | 0.50-3.00 |
| n-tert butylbenzothiazole 2-sulphenamide/tetraethylthiuram disulphide | TBBS/TMTD | 0.00-0.50 |
| Activator (Chemical type) | | |
| Active ZnO | ZnO | 0.10-1.00 |
| Accelerators (Chemical type) | | |
| Zinc diethiocarbamate/Zinc dibutyldithiocarbamate | ZDEC/ZDBC | 0.10-1.00 |
| Zinc-2-mercaptobenzothiazole/Sodium dibutyldithiocarbamate | ZMBT/SDBC | 0.01-0.50 |
| Diisopropyl xanthogen polysulphide | | 0.10-0.60 |
| Anti-oxidants (Chemical type) | | |
| 4 & 5 methyl-2-mercaptobenzimidazole/Butylated p-cresol & dicyclopentadiene | | 0.80-2.5 |
| Surfactants/Emulsifiers/Wetting agents (Chemical type) | | |
| Sodium salts of naphthalenesulphonic acid/Sodium lauryl sulfate | | 0.10-0.80 |
| Sodium linear alkylbenzene sulfonate/Potassium caprylate | | 0.10-1.00 |
| Sodium linear alkyl benzene sulfonate & sodium lauryl ether sulfate | Teepol LD I-21 | 0.01-0.10 0.00-0.10 |

In embodiments, the present disclosure further provides methods of forming a synthetic polyisoprene latex article. In embodiments, methods comprise dipping a coagulant coated former in blend of the above-described pre-vulcanized and un-vulcanized synthetic polyisoprene aqueous latex emulsion composition at least once to form a layer of latex film with individual particles of pre-vulcanized and un-vulcanized synthetic polyisoprene on the surface of the former. The former can be any suitable former as is known in the art. In embodiments, the present disclosure provides compositions useful for layering onto formers for gloves. In embodiments, the methods comprise allowing the thin layer of latex film formed on the surface of the former to dry after each dip. The spaces between the particles decrease as the layer dries. After the last layer of latex film is dry in the case of multiple dips of the former into the synthetic polyisoprene latex emulsion, the method further comprises post-vulcanizing the thin latex film on the former. The film can be post-vulcanized by heating the film, e.g., to about 100 to 150° C. for about 10 to 30 min. During this period, the inter-particle regions are crosslinked. The intra-particle regions also undergo further crosslinking, producing a more homogeneous latex product. Then, the methods comprise stripping the latex film from the former. In the absence of pre-vulcanization of the synthetic polyisoprene particles, crosslinking predominantly occurs in the periphery of the synthetic polyisoprene particles, resulting in weak particles.

Table 4 below shows an embodiment of a process sequence for making articles of the present disclosure.

TABLE 4

The thickness of the glove or condom film is controlled by coagulant concentration, the total solids of latex in the dip tank, and the speed of the former

TABLE 4-continued

Drying after dipping before leaching (60° C.-100° C.)
Leaching (50-80° C. 1-3 min)
Drying of the film in the cure ovens (105° C.-140° C.)
Post oven leaching at temperature (70° C.-90° C.: 1-2 min)
Stripping and drying
Post processing & packing The sequence of dipping for the gloves or condoms using surfactant stabilized, pre-vulcanized synthetic polyisoprene latex composition of the present disclosure is typically within a 5 day period, the average life-time of the synthetic polyisoprene latex emulsion tank. In embodiments, a glove former or condom former is dipped in the coagulant tank first and then in the latex emulsion tank. The thickness of the glove or condom film is controlled by the coagulant concentration, total solids of the latex emulsion and the speed of the movement of the former through the dip tank. In some glove embodiments, the latex film is dried at 60-80° C. before dipping in to the leach tank for 1 to 3 min and then dipped through polymer coating primer before being dipped in to a non-tacky polymer coating before the film is rolled at the free end to create a bead on to the glove.

In embodiments, films thus formed are cured in the ovens at 100-150° C. for 30-35 min., post oven leached at 70-80° C. and then dipped in the slurry tank for 1 to 2 min. before being stripped from the former at the stripping station. The latex articles thus produced display comparable unaged tensile strength and modulus to the latex articles typically produced, for example, using DPG as a rubber accelerator in the latex formulation, however latex articles of the present disclosure exhibit increases in tensile strength over aging at 70° C. for seven days (accelerated aging conditions) and 50° C. for 90 days in contrast to, polyisoprene latex films produced using only pre-vulcanized polyisoprene synthetic latex composition without blending with un-vulcanized polyisoprene latex component, where tensile strength typically drops over aforementioned aging conditions.

Figure 2:
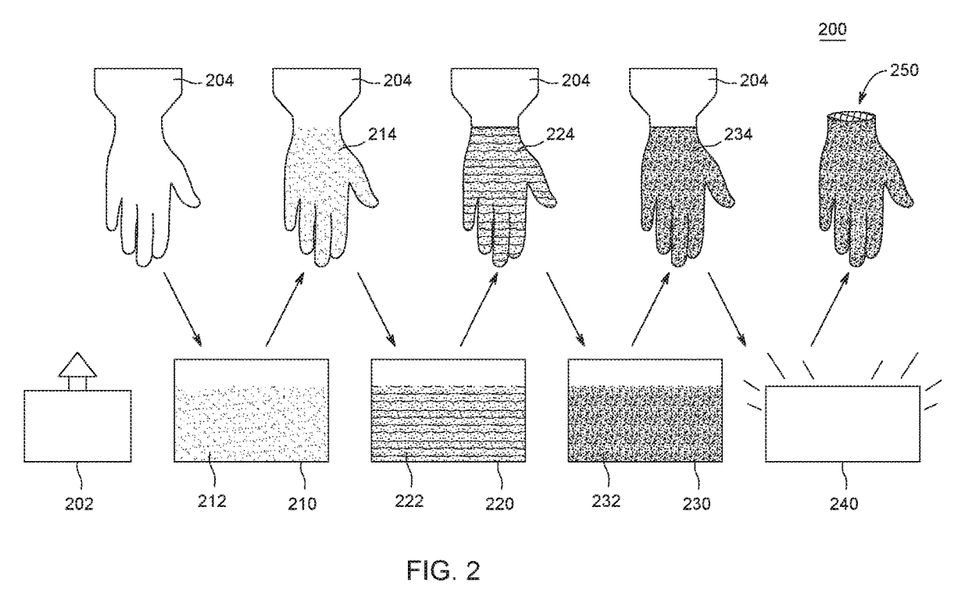
FIG. 2 depicts an apparatus used to manufacture the articles of the present disclosure.

FIG. 2 depicts an apparatus 200 used to manufacture a glove 250, according to embodiments of the present disclosure. The apparatus 200 comprises a controller 202, which controls, for example, production line equipment, such as electronic circuits for controlling robots that deliver at least one former 204 (glove former or condom former) to tanks 210, 220, 230, and an oven 240. A former 204 is shown in the shape of a glove. In embodiments, the former 204 may be dipped into a tank 210 containing a coagulant 212, which becomes disposed on the former 204 as coagulant particles 214. The former 204 is optionally shaped as a condom. In some embodiments, the former 204 having the coagulant 212 disposed thereon is removed from the coagulant tank 210 and allowed to dry.

In embodiments, the former 204 having the coagulant particles 212 disposed thereon as coagulant particles 214 is then dipped into a tank 220, containing a polymeric, elastomeric, or latex composition for coating comprising a blend of a synthetic polyisoprene material 222 to form a layer atop the former, wherein the blend of a synthetic polyisoprene material 222 comprises a pre-vulcanized polyisoprene component and non-prevulcanized polyisoprene component as described herein. The former 204 now has an uncured composition 222 of the present disclosure disposed thereon as a first layer or coating 224. This first layer or coating may optionally be dried and/or subjected to one or more additional dips into tank 220. Optionally, the former 204 is dipped into a leach tank 230 as described above including leaching constituents 232.

In embodiments, the former 204 may then delivered to an oven 240, wherein the first polymeric layer or coating 224 or leached layer 234 are cured with heat, as discussed above, to form a film of glove 250. In embodiments, curing the layer is performed to form a cured synthetic polyisoprene film with pre-vulcanized polyisoprene component and non-prevulcanized polyisoprene component bonded by monosulfidic and/or di-sulfidic, and poly-sulfidic crosslinks, wherein the poly-sulfidic crosslinks are present in an amount of 60 to 79 percent of the total amount of crosslinks in the film. In embodiments, films so formed have enhanced tensile strength upon aging compared to its unaged value.

In some embodiments, a method of making a synthetic polyisoprene article includes: dipping a former into a polymeric, elastomeric, or latex coating composition comprising a blend of a synthetic polyisoprene material to form a layer atop the former, wherein the blend of a synthetic polyisoprene material comprises a pre-vulcanized polyisoprene component and non-prevulcanized polyisoprene component; and curing the layer to form a cured synthetic polyisoprene film with pre-vulcanized polyisoprene component and non-prevulcanized polyisoprene component bonded by mono-sulfidic and/or di-sulfidic, and poly-sulfidic crosslinks, wherein the poly-sulfidic crosslinks are present in an amount of 60 to 79 percent of the total amount of crosslinks in the film. In embodiments, the film has enhanced tensile strength upon aging compared to its unaged value. In some embodiments, the crosslinks are present in an amount of 64 to 76 percent of the total amount of crosslinks in the film. In some embodiments, prior to dipping the former, the methods comprises coating a former with a coagulant solution. Some embodiments further comprise forming the pre-vulcanized polyisoprene component to comprise a predetermined degree of vulcanization. Some embodiments further comprise forming the pre-vulcanized polyisoprene component to a degree of vulcanization characterized by a toluene swelling index between 200% and 110%. Some embodiments further comprise forming the pre-vulcanized polyisoprene component by heating to a temperature in the amount of 25 degrees Celsius to 80 degrees Celsius.

In some embodiments, a glove or condom, formed by the method described above is provided. In embodiments, the glove or condom have a retained tensile strength of at least 95% after aging for at least seven days. In embodiments, the glove or condom further comprise a cured blend composition comprising pre-vulcanized synthetic polyisoprene particles present in an amount of 65 to 95 percent weight of the total blend composition and non-prevulcanized synthetic polyisoprene particles present in an amount of 5 to 35 percent weight of the total blend composition.

In embodiments, the tensile property of the glove or condom produced is measured using ASTM D3577. In embodiments, articles such as gloves or condoms show an increased tensile strength when comparing an aged article (70 degrees Celsius for 7 days) to an unaged version thereof. For example the aged article may be indicate a test result of 1-5 UTS/MPa, including 1, 2, 3, 4, or 5 UTS/MPa higher than its unaged equivalent. For example, if unaged tensile strength of an article is 19 UTS/MPa, then the aged article may show 20-24 UTS/MPa.

Tear strength is a very important property of a glove or condom and it was measured and compared with that of the synthetic polyisoprene glove produced using a latex formulation that comprised of an accelerator package containing thiourea/thiuram disulphide as an accelerator. Tear strength was measured using ASTM D624: 2000 method. In embodiments, articles of the present disclosure show a median tear strength (N/mm) between about 25 and 30.

In embodiments, the present disclosure relates to a synthetic polyisoprene elastomeric article including: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent of the total amount of crosslinks in the cured blend composition. In embodiments, an amount of the poly-sulfidic crosslinks in the cured blend composition is substantially retained upon aging, for example, the amount of poly-sulfidic crosslinks do not substantially decrease such as decrease more than 30%, more than 15%, or more than 12%, for example upon ageing or when subjected to accelerated ageing as described herein. In embodiments, a crosslink density of the cured blend composition increases by at least 20% upon aging, such as about 20% to about 30%, or 20% to about 25%. In embodiments, the tensile strength of the cured blend composition increases upon aging. For example the tensile strength of the cured blend composition may increases upon aging by 1-5 UTS/MPa, 2-5 UTS/MPa, 3-5 UTS/MPa, or 4-5 UTS/MPa. In embodiments, the cured blend composition comprises pre-vulcanized synthetic polyisoprene particles present in an amount of 65 to 95 percent weight of the total blend composition and non-prevulcanized synthetic polyisoprene particles present in an amount of 5 to 35 percent weight of the total blend composition. In embodiments, the pre-vulcanized synthetic polyisoprene particles are vulcanized to a predetermined degree characterized by a toluene swelling index between 200% and 110%. In embodiments, the cured blend composition is formed with partially pre-vulcanized synthetic polyisoprene particles characterized by a toluene swelling index between 200% and 110%.

In embodiments, the cured blend composition is formed with partially pre-vulcanized synthetic polyisoprene particles heated to a temperature in the amount of 25 degrees Celsius to 80 degrees Celsius prior to contacting the non-prevulcanized synthetic polyisoprene particles. In embodiments, the cured blend composition comprises pre-vulcanized synthetic polyisoprene particles and the non-prevulcanized synthetic polyisoprene particles bonded through intra-polyisoprene particle crosslinks and inter-polyisoprene crosslinks, wherein the amount of inter-polyisoprene crosslinks and crosslink density increases upon aging. In embodiments, the cured blend composition comprises a crosslink density in the amount of $9.0 \times 10^{-5}$ to $12 \times 10^{-5}$ n mol/cm$^3$ prior to aging. In embodiments, the poly-sulfidic crosslinks comprise at least 3 sulfur atoms. In embodiments, the poly-sulfidic crosslinks are present in an amount of 70 to 76 percent of the total crosslinks in the cured blend composition, and wherein the tensile strength of the cured blend composition increases upon aging.

In some embodiments, the degree of vulcanization of the pre-vulcanized polyisoprene component varies from 200% to 110% as measured using toluene swelling index and the blending percentage of non-prevulcanized component to prevulcanized component varies from 10% to 50% by weight of the total composition. In some embodiments, an article is formed from the composition described herein, wherein the article has an unaged ultimate tensile strength of at least 18 MPa and aged ultimate tensile strength of at least 22 Mpa after accelerated aging at 70° C. for 7 days, measured according to ASTM D3577. In some article embodiments, the article has a minimum tear strength of 30 N/mm measured as per ASTM D624. In some embodiments, the tear strength increases over aforementioned aging conditions by a minimum of 5 (N/mm).

In some embodiments, the present disclosure relates to a synthetic polyisoprene elastomeric article comprising: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 to 79 percent or 64 to 76 percent of the total amount of crosslinks in the cured blend composition. In embodiments, the pre-vulcanized synthetic polyisoprene particles, prior to being mixed with the non-prevulcanized synthetic polyisoprene particles comprise zinc diisononyl dithiocarbamate. In embodiments, the pre-vulcanized synthetic polyisoprene particles, prior to being mixed with the non-prevulcanized synthetic polyisoprene particles comprises di-isopropyl xanthogen polysulfide. In embodiments, the pre-vulcanized synthetic polyisoprene particles, prior to being mixed with the non-prevulcanized synthetic polyisoprene particles comprise zinc diisononyl dithiocarbamate, and di-isopropyl xanthogen polysulfide. In embodiments, the pre-vulcanized synthetic polyisoprene particles comprises zinc diisononyl dithiocarbamate in an amount of 0.75 parts by weight of the pre-vulcanized synthetic polyisoprene particles (as dry/active content (dry wt./(kg)), and di-isopropyl xanthogen polysulfide in an amount of 2.0 parts by weight of the of the pre-vulcanized synthetic polyisoprene particles. In some embodiments, zinc diisononyl dithiocarbamate in the pre-vulcanized synthetic polyisoprene particles comprises a dispersion (35%) and is supplied as ARBESTAB Z brand zinc diisononyl dithiocarbamate.

In some embodiments, the present disclosure relates to a synthetic polyisoprene elastomeric article comprising: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 60 percent to 79 percent, 64 to 76 percent of the total amount of crosslinks in the cured blend composition. In embodiments, the pre-vulcanized synthetic polyisoprene particles, prior to being mixed with the non-prevulcanized synthetic polyisoprene particles (at a time before curing) comprise zinc diisononyl dithiocarbamate, wherein zinc diisononyl dithiocarbamate is present in an amount of 0.75 parts by weight of the pre-vulcanized synthetic polyisoprene particles (as dry/active content or dry wt./(kg)), and di-isopropyl xanthogen polysulfide is present in an amount of 2.0 parts by weight of the of the pre-vulcanized synthetic polyisoprene particles. In some embodiments, zinc diisononyl dithiocarbamate comprises a dispersion (35%) and is supplied as ARBESTAB Z brand zinc diisononyl dithiocarbamate. In embodiments, the non-prevulcanized synthetic polyisoprene particles are present in an amount of 100 phr prior to being mixed with the pre-vulcanized synthetic polyisoprene particles. In embodiments, and di-isopropyl xanthogen polysulfide is provided in an emulsion comprising di-isopropyl xanthogen polysulfide in combination with potassium hydroxide, and fatty acid such as PALMAC 750 brand fatty acid.

In some embodiments, the present disclosure relates to a synthetic polyisoprene elastomeric article comprising: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by mono-sulfidic and/or di-sulfidic, and poly-sulfidic crosslinks, wherein the poly-sulfidic crosslinks are present in an amount of 64 to 76 percent of the total amount of crosslinks in the cured blend composition. In embodiments, the pre-vulcanized synthetic polyisoprene particles, prior to being mixed with the non-prevulcanized synthetic polyisoprene particles comprise zinc diisononyl dithiocarbamate, wherein zinc diisononyl dithiocarbamate is present in an amount 0.10-1.0 phr (of the pre-vulcanized synthetic polyisoprene particles) and di-isopropyl xanthogen polysulfide is present in an amount of 0.10 to 0.6 phr (of the of the pre-vulcanized synthetic polyisoprene particles). In embodiments, the non-prevulcanized synthetic polyisoprene particles are present in an amount of 100 phr prior to being mixed with the pre-vulcanized synthetic polyisoprene particles. In embodiments, the cured blend composition comprises a crosslink density in an amount of $9.0 \times 10^{-5}$ to $12 \times 10^{-5}$ n mol/cm$^3$ prior to aging, or an average molecular weight between crosslinks in the amount of 8053 and 9711.

In some embodiments, the present disclosure relates to a method of making a synthetic polyisoprene article comprising: dipping a former into a polymeric, elastomeric, or latex coating composition comprising a blend of a synthetic polyisoprene material to form a layer atop the former, wherein the blend of a synthetic polyisoprene material comprises a pre-vulcanized polyisoprene component and non-prevulcanized polyisoprene component; and curing the layer to form a cured synthetic polyisoprene film with pre-vulcanized polyisoprene component and non-prevulcanized polyisoprene component bonded by mono-sulfidic and/or di-sulfidic, and poly-sulfidic crosslinks, wherein the poly-sulfidic crosslinks are present in an amount of 60 to 79 percent, or 64 to 76 percent of the total amount of crosslinks in the film. In embodiments, the film has enhanced tensile strength upon aging compared to its unaged value. In embodiments, prior to curing, the method comprises forming a blend of a synthetic polyisoprene material comprising a pre-vulcanized polyisoprene component and non-prevulcanized polyisoprene component, wherein in embodiments, the pre-vulcanized polyisoprene component comprises zinc diisononyl dithiocarbamate, and di-isopropyl xanthogen polysulfide. In embodiments, the pre-vulcanized polyisoprene component comprises zinc diisononyl dithiocarbamate, wherein zinc diisononyl dithiocarbamate is present in an amount 0.10-1.0 phr (of the pre-vulcanized polyisoprene component) and di-isopropyl xanthogen polysulfide is present in an amount of 0.10 to 0.6 phr (of the of the pre-vulcanized polyisoprene component). In embodiments, the pre-vulcanized polyisoprene component comprises a predetermined degree of vulcanization prior to mixing with the non-pre-vulcanized polyisoprene component. In embodiments, the pre-vulcanized polyisoprene component is pre-vulcanized to a degree of vulcanization characterized by a toluene swelling index between 200% and 110%. In embodiments, the cured blend composition comprises or consists of a crosslink density in an amount of $9.0 \times 10^{-5}$ to $12 \times 10^{-5}$ n mol/cm$^3$ prior to aging, or an average molecular weight between crosslinks in the amount of 8053 and 9711.

In some embodiments, the present disclosure relates to a synthetic polyisoprene elastomeric article comprising: a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by poly-sulfidic crosslinks, wherein the poly-sulfidic crosslinks are present in an amount of 60 to 79 percent of the total amount of crosslinks in the cured blend composition. In embodiments, the pre-vulcanized polyisoprene particles is pre-vulcanized to a degree of vulcanization characterized by a toluene swelling index between 200% and 110%. In embodiments, the cured blend composition comprises or consists of a crosslink density in an amount of $9.0 \times 10^{-5}$ to $12 \times 10^{-5}$ n mol/cm$^3$ prior to aging, and/or an average molecular weight between crosslinks in the amount of 8053 and 9711. In embodiments, the pre-vulcanized polyisoprene component comprises zinc diisononyl dithiocarbamate, wherein zinc diisononyl dithiocarbamate is present in an amount 0.10-1.0 phr (of the pre-vulcanized polyisoprene component) and di-isopropyl xanthogen polysulfide is present in an amount of 0.10 to 0.6 phr (of the of the pre-vulcanized polyisoprene component) prior to blending with the non-prevulcanized synthetic polyisoprene particles, and prior to curing.

Materials and Methods
Toluene Swell Test for Precure Compounds
I. Determination of Toluene Swell Index (TSI) of Natural Rubber compounded latex
1. Prepare calcium nitrate/diacell solution.
2. Dip a piece of white cardboard (approximately size 3.5 cm×8.5 cm) into the calcium nitrate/diacell solution for 10 seconds and remove slowly.
3. Scrape the excess solution off the card using a glass rod.
4. Dip the card into the latex sample for 10 seconds and slowly withdraw.
5. Allow the latex to air dry for 2 minutes. Cover bottom side with card board and lay it on the cutting block. Cut a 1 inch disc from the card with a punch hole.
6. Take card board off, a carefully peel the top latex disc off the card and drop it into Petri dish containing toluene then, discard the bottom disc cards.
7. Allow the disc to swell until equilibrium is achieved (40 minutes).
8. Place the Petri dish on a calibrated steel ruler and measure the swollen diameter.
9. Calculate the percent toluene swell as follows:

$$@=(SF-SO)\times 100\%$$
So'
where SF=swollen diameter
and SO=initial diameter (1 inch)

II. Determination of Toluene Swell Index (TSI) of synthetic polyisoprene (Pi) compounded latex
1. Prepare 800 g/L (80% w/v concentration) calcium nitrate solution.
2. Dip a piece of white card board (approximately 3.5 cm×8.5 cm) into solution up to 7 cm mark for 10 seconds and remove slowly to ensure an even and thin layer of calcium nitrate is obtained.
3. Drip off excess solution from the card board.
4. Dry card board in 100 degrees Celsius oven for 10 minutes.
5. Dip the card board into the latex sample for 10 seconds in PI Isolex and 15 seconds in PI Kraton and withdraw slowly.
6. Allow cardboard to dry at 50 degrees Celsius in an oven for 15 minutes.
7. Take card board off, carefully peel the latex disc off the card board and drop it into petri dish containing toluene (approximately 20-30 ml), with base covered with 60 mesh Nylon.
8. Shake the Nylon filter gently immediately after dropping the latex disc into Toluene to ensure the latex disc is not sticking to the base of the petri dish.
9. Ensure the latex disc is fully immersed in toluene.
10. Allow disc to swell until equilibrium is achieved (1 hr).
11. Place the petri dish on a calibrated steel ruler and measure the swollen diameter.
12. Duplicate the test and record average results.

Card board suitable for use herein includes cardboard substance of 350 g/m$^2$, bulk 1.25 cc/gms, 437 microns, taber stiffness (MD 160 CD 70).

Examples

I. Crosslink Quantitative Analysis
Investigation of a control synthetic polyisoprene glove and synthetic polyisoprene glove in accordance with the present disclosure was conducted on gloves supplied and aged. Part of the glove for both samples was aged within their paper wrappers in an oven with circulating air at 70 degrees Celsius for 7 days.

Volume Swelling
Five samples, (a nominal 10 mm in width) were cut from each of the aged and unaged gloves for swelling in toluene. Each sample was measured using a travelling microscope with Vernier scale with 0.01 mm graduations (L1). Samples were then immersed in AR Grade toluene and left to swell in the dark overnight in a closed vial. The swollen length was measure with the glove samples under the toluene (L2). The swelling Vr (volume fraction in the swollen sample) was calculated from the cube of the ratios L2/L1. The crosslink density of each sample was calculated from the average Vrs of the five values and the molecular weight between the crosslinks calculated from these values. The change in length of the samples was chosen for the measure of swelling (rather than change in weight) on account of a known difficulty of determining swelling on thin samples: ensuring that the surfaces are dry yet not allowing any solvent evaporation from the sample is not easy to achieve and introduces a greater uncertainty in the values measured.

Calculations

Crosslink density, n, and molecular weight between crosslinks, Mc, were calculated using the equation below:

$$n = -1/V_s \times (\mathrm{Ln}(1-Vr) + Vr + xVr^2)/(Vr^{1/3} - Vr/2)$$

Mc=rubber density/n
where Vr is the volume fraction of rubber, Vs is the molar volume of the solvent (106.3) and x is the polymer-solvent interaction parameter (0.39).

TABLE 5

Results

| | Control (unaged) | Control Aged | Composition of the present disclosure (unaged) | Composition of the present disclosure (aged) |
|---|---|---|---|---|
| L2/L1 ($Vr^{1/3}$) | 0.566 | 0.578 | 0.548 | 0.564 |
| Vr | 0.181 | 0.193 | 0.165 | 0.179 |
| n mol/cm$^3$ | 11.7 × 10$^{-5}$ | 13.5 × 10$^{-5}$ | 9.47 × 10$^{-5}$ | 11.4 × 10$^{-5}$ |
| Mc | 7865 | 6827 | 9711 | 8053 |

Upon aging the composition of the present disclosure shows a crosslink density increase by 20%.

Network Visualization

Pieces of the gloves were extracted in hot acetone overnight to remove any material which might interfere with the polymerization. Pieces of each sample were then swollen to equilibrium in styrene solution containing 1 wt % benzoyl peroxide initiator and 2 wt % dibutylphthalate plasticizer to aid sectioning. The swollen films were then placed in capsules with excess styrene solution and heated at 50 degrees Celsius until the styrene had fully polymerized. The styrene swollen, polymerized samples were sectioned by ultramicrotomy at room temperature with a diamond knife. The ultra-thin sections were collected on a water-filled trough, and then relaxed by exposure to xylene vapor to remove any compression caused by the sectioning process. The sections were transferred to TEM grids and then stained in osmium tetroxide vapor for 7 minutes. Osmium tetroxide reacts with carbon-carbon double bonds and therefore increases the electron density of polymers containing unsaturated groups. Thus it makes unsaturated polymers such as polyisoprene appear dark in the TEM relative to polystyrene. (The expanded uncertainty (k factor 2 for 95% confidence) on the scalebar dimension is +10% in all TEM micrographs). Examples of TEM micrographs of osmium tetroxide treated articles in accordance with the present disclosure are shown in FIG. 1B.

TEM Interpretation

The formulation of the present disclosure shows interparticle crosslink density to be higher in the aged sample than the unaged sample.

2. Crosslink Qualitative Analysis

Investigation of a control synthetic polyisoprene glove and synthetic polyisoprene glove in accordance with the present disclosure was conducted on gloves supplied and aged.

Experimental

The method measure the crosslink density in the untreated glove by means of volume swelling in hexane before and after treatment with a thiol-amine chemical probe reagent that breaks the polysulfide crosslinks (e.g. crosslinks with three or more sulfur atoms). The swelling method gives the physical crosslink density of the rubber using the Flory-Rehner equation. (See e.g., P. J. Flory and J. Rehner, *J. Chem. Phys.*, 11, 1943, 521). This value includes physical entanglements. The chemical crosslink density was then calculated using the Moore, Mullins, Watson correlation (See L. Mullins, *J. Appl. Polym. Sci.*, 2, 1959,1), assuming the molecular weight $M_n$ of 1,000,000. Given the solvent for swelling is not the same as for the probe treatment, two solvent exchanges were required. The hexane-natural rubber system has an established interaction parameters. See e.g, G. M Bristow and W. F. Watson, *Trans. Faraday Soc.*, 54, 1958, 1731. As the glove films were translucent, the swelling was determined to 0.01 mmb y measuring the samples using a travelling microscope. Strips, approximately 10 mm wide, were cut from the gloves using a twin-bladed cutter. From these samples were prepared, making small cuts in each for identification purposes. The samples were measured across the 10 mm direction: L1. The samples were then swollen in n-hexane overnight in the dark and re-measured while in the solvent: L2. Next the samples were transferred to the reaction tube under a nitrogen atmosphere. The hexane was drained off and replaced with degassed n-heptane. After approximately 10 min. the n-heptane was drained off the samples and fresh n-heptane added (5 ml/sample). After an additional 30 min., the reaction mixture was added (2.5 ml/sample). (The reaction mixture comprised 1.2M piperidine and 1.2M propane-2-thiol in degassed n-heptane. The final concentration being 0.4M solutions of the thiol and amine). The system was stored closed under a nitrogen atmosphere for 2 hours at 25 degrees Celsius. After 2 hours the reaction mixture was drained off and replaced with degassed n-hexane (ca 3 ml solvent/sample) which was left for 10 minutes before draining the solvent off. This washing process was repeated 6 more times. After the final washing, the samples were stored in individual nitrogen-flushed sample bottles with ca 15 ml 1-hexane overnight and then re-measured under the solvent: L3. The physical crosslink density was determined by using the Flory-Rehner equation.

$$2p\ n_{Phys} V_s v_r^{1/3} = -\ln(1-v_r) - v_r - X\ Vr^2$$

wherein
$V_s$ is the molar volume of the solvent (130.77)
Vr is the volume fraction of rubber in the swollen samples (Vr=(L2/L1)$^3$ or (L3/L1)$^3$, as appropriate).
X is the polymer solvent interaction parameter (0.474$^{(3)}$)
p is the rubber density (0.92).
The chemical crosslink density is then calculated from this $n_{Phys}$ using the Moore Mullins Watson correlation $$pRTn_{Phys} = (pRTn_{chem} + 0.78 \times 10^6)(1 - 1.15/M_n n_{chem})$$

wherein
$M_n$ is the number average molecular weight of the NR (not know so 1,000,000 is used).

TABLE 6

Results $v_r$

| | Control | Control Aged | Composition of the present disclosure (unaged) | Composition of the present disclosure (aged) |
|---|---|---|---|---|
| $v_r$ swollen | 0.264 | 0.268 | 0.244 | 0.266 |
| $v_r$ after probe treatment | 0.206 | 0.249 | 0.195 | 0.138 |

TABLE 7

Physical crosslink density $n_{Phys}$

| | Control | Control (aged) | Composition of the present disclosure (unaged) | Composition of the present disclosure (aged) |
|---|---|---|---|---|
| $n_{Phys}$ mm/100 g | 6.13 | 7.66 | 5.03 | 6.29 |
| $n_{Phys}$ after probe treatment mm/100 g | 3.22 | 5.27 | 2.82 | 2.06 |

TABLE 8

Chemical crosslink density $n_{chem}$

| | Control | Control (aged) | Composition of the present disclosure (unaged) | Composition of the present disclosure (aged) |
|---|---|---|---|---|
| $N_{chem}$ mm/100 g | 3.0 | 4.5 | 1.9 | 3.1 |
| $N_{chem}$ after probe treatment mm/100 g | 0.59 | 2.16 | 0.47 | 1.13 |

TABLE 9

Crosslink type

| | Control | Control (aged) | Composition of the present disclosure (unaged) | Composition of the present disclosure (aged) |
|---|---|---|---|---|
| Poly-sulfidic, % of total | 80 | 52 | 76 | 64 |
| Mono and di Sulfidic, % of total | 20 | 48 | 24 | 36 |

Upon review of the data above, it is likely the majority of the $n_{Phys}$ are entanglements. The proportion of the mono and di sulfide crosslinks increases more in the control glove.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention, unless otherwise claimed. No language in the specification should be construed as indicating any non-claimed element as essential to the practice of the invention.

The invention claimed is:

1. A synthetic polyisoprene elastomeric article comprising:
a cured blend composition of pre-vulcanized synthetic polyisoprene particles and non-prevulcanized synthetic polyisoprene particles, wherein the pre-vulcanized synthetic polyisoprene particles and the non-prevulcanized synthetic polyisoprene particles are bonded by sulfidic crosslinks comprising poly-sulfidic crosslinks, wherein the poly-sulfidic crosslinks are present in an amount of 60 to 79 percent of a total amount of crosslinks in the cured blend composition; and
wherein the cured blend composition comprises pre-vulcanized synthetic polyisoprene particles present in an amount of 65 to 95 percent weight of the cured blend composition and non-prevulcanized synthetic polyisoprene particles present in an amount of 5 to 35 percent weight of the cured blend composition.

2. The synthetic polyisoprene elastomeric article of claim 1, wherein an amount of the poly-sulfidic crosslinks in the cured blend composition does not decrease by more than 30% aging for at least seven days at 70 degrees Celsius.

3. The synthetic polyisoprene elastomeric article of claim 2, wherein a tensile strength of the cured blend composition increases upon aging for at least seven days at 70 degrees Celsius.

4. The synthetic polyisoprene elastomeric article of claim 2, wherein a crosslink density of the cured blend composition increases by at least 20% upon aging for at least seven days at 70 degrees Celsius.

5. The synthetic polyisoprene elastomeric article of claim 1, wherein a tensile strength of the cured blend composition increases upon aging for at least seven days at 70 degrees Celsius.

6. The synthetic polyisoprene elastomeric article of claim 1, wherein the cured blend composition comprises pre-vulcanized synthetic polyisoprene particles present in an amount of 75 to 95 percent weight of the cured blend composition and non-prevulcanized synthetic polyisoprene particles present in an amount of 5 to 25 percent weight of the cured blend composition.

7. The synthetic polyisoprene elastomeric article of claim 1, wherein the pre-vulcanized synthetic polyisoprene particles are vulcanized to a predetermined degree characterized by a toluene swelling index between 200% and 110%.

8. The synthetic polyisoprene elastomeric article of claim 1, wherein the pre-vulcanized synthetic polyisoprene particles are vulcanized to a predetermined degree characterized by a toluene swelling index between 200% and 110%.

9. The synthetic polyisoprene elastomeric article of claim 1, wherein the cured blend composition is formed with partially pre-vulcanized synthetic polyisoprene particles heated to a temperature in the amount of 25 degrees Celsius to 80 degrees Celsius prior to contacting the non-prevulcanized synthetic polyisoprene particles.

10. The synthetic polyisoprene elastomeric article claim 1, wherein the cured blend composition comprises pre-vulcanized synthetic polyisoprene particles and the non-prevulcanized synthetic polyisoprene particles bonded through intra-polyisoprene particle crosslinks and inter-polyisoprene crosslinks, wherein an amount of inter-polyisoprene crosslinks and a crosslink density increases upon aging for at least seven days at 70 degrees Celsius.

11. The synthetic polyisoprene elastomeric article claim 1, wherein the cured blend composition comprises a crosslink density in an amount of $9.0 \times 10^{-5}$ to $12 \times 10^{-5}$ n mol/cm$^3$ prior to aging for at least seven days at 70 degrees Celsius, or an average molecular weight between crosslinks in the amount of 8053 and 9711.

12. The synthetic polyisoprene elastomeric article of claim 1, wherein the poly-sulfidic crosslinks are present in an amount of about 64 to about 76 percent of the total amount of crosslinks in the cured blend composition, and wherein a tensile strength of the cured blend composition increases upon aging for at least seven days at 70 degrees Celsius.

13. The synthetic polyisoprene elastomeric article of claim 1, which article is a condom.

14. The synthetic polyisoprene elastomeric article of claim 1, which article is a glove.

15. A method of making a synthetic polyisoprene article comprising:
dipping a former into a polymeric, elastomeric, or latex coating composition comprising a blend of a synthetic polyisoprene material to form a layer atop the former, wherein the blend of a synthetic polyisoprene material comprises a pre-vulcanized polyisoprene component and non-prevulcanized polyisoprene component; and
curing the layer to form a cured synthetic polyisoprene film with pre-vulcanized polyisoprene component and non-prevulcanized polyisoprene component bonded by mono-sulfidic and/or di-sulfidic, and poly-sulfidic crosslinks, wherein the poly-sulfidic crosslinks are present in an amount of 60 to 79 percent of a total amount of crosslinks in the film; wherein the cured synthetic polyisoprene film comprises pre-vulcanized synthetic polyisoprene particles present in an amount of 65 to 95 percent weight of the cured synthetic polyisoprene film, and non-prevulcanized synthetic polyisoprene particles present in an amount of 5 to 35 percent weight of the cured synthetic polyisoprene film.

16. The method of claim 15, further comprising forming the pre-vulcanized polyisoprene component to comprise a predetermined degree of vulcanization characterized by a toluene swelling index between 200% and 110%.

17. A condom, formed by the method of claim 15.

18. The condom of claim 17, wherein the condom has a retained tensile strength of at least 95% after aging for seven days at 70 degrees Celsius.

19. A glove, formed by the method of claim 15.

20. The glove of claim 19, wherein the glove has a retained tensile strength of at least 95% after aging for seven days at 70 degrees Celsius.

* * * * *